(12) United States Patent
Moter

(10) Patent No.: US 10,508,302 B2
(45) Date of Patent: Dec. 17, 2019

(54) CONTROL PREPARATION FOR FISH METHODS IN MICROBIOLOGY

(71) Applicant: Charité Universitätsmedizin Berlin, Berlin (DE)

(72) Inventor: Annette Moter, Berlin (DE)

(73) Assignee: CHARITE UNIVERSITATSMEDIZIN BERLIN, Berlin (DE)

( * ) Notice: Subject to any disclaimer, the term of this patent is extended or adjusted under 35 U.S.C. 154(b) by 0 days.

(21) Appl. No.: 15/546,328

(22) PCT Filed: Jan. 27, 2016

(86) PCT No.: PCT/EP2016/051630
§ 371 (c)(1),
(2) Date: Jul. 26, 2017

(87) PCT Pub. No.: WO2016/120295
PCT Pub. Date: Aug. 4, 2016

(65) Prior Publication Data
US 2019/0024157 A1    Jan. 24, 2019

(30) Foreign Application Priority Data
Jan. 27, 2015   (DE) .................. 10 2015 101 168

(51) Int. Cl.
| C12Q 1/68 | (2018.01) |
| C12N 15/11 | (2006.01) |
| C12Q 1/6841 | (2018.01) |
| C12Q 1/689 | (2018.01) |

(52) U.S. Cl.
CPC .......... *C12Q 1/6841* (2013.01); *C12Q 1/689* (2013.01); *C12N 15/11* (2013.01)

(58) Field of Classification Search
None
See application file for complete search history.

(56) References Cited

PUBLICATIONS

Mahmoud K K et al.: "Detection of Acidithiobacillus ferrooxidans in acid mine drainage environments using florescent in situ hybridization (FISH)", Journal of Microbiological Methods, Elsevier, Amsterdam, NL, vol. 61, no1. 1, Apr. 1, 2005, pp. 33-45.
Thayanukul P et al: "Concentration-dependent response of estrone-degrading bacterial community in activated sludge analyzed by microautoradiography-fluorescence in situ hybridization", Water Research, Elsevier, Amsterdam, NL, vol. 44, No. 17, Sep. 1, 2010, pp. 4878-4887.
Lischewski A et al: "Specific Detection of Candida Albicans and Candida Tropicalis by Fluorescent in Situ Hybridization with an 18S RRNA-Targeted Oligonucleotide Probe", Microbiology, Society for General Microbiology, GB, vol. 142, No. 10, Oct. 1, 1996, pp. 2731-2740.
Akihiro Ohnishi et al.: "Rapid detection and quantification methodology for genusas a hyrdrogen producer in a hydrogen fermentation system", International Journal of Hydrogen Energy, Elsevier Science Publshers B.V., Barking, GB, vol. 37, No. 3, Oct. 22, 2011, pp. 2239-2247.
Boye M et al: "Fusobacterium necrophorum determined as abortifacient in sheep by laser capture microdissection and fluorescence in situ hybridization", Molecular and Cellular Probes, Academic Press, London, GB, vol. 20, No. 6, Dec. 1, 2006, pp. 330-336.
P.T. Sunde: "Fluorescence in situ hybridization (FISH) for direct visualization of bacteria in periapical lesions of asymptomatic root-filled teeth", Microbiology, vol. 149, No. 5, May 1, 2003, pp. 1095-1102.
Moter A et al: "Fluorescence in situ hybridization (FISH) for direct visualization of microorganisms", Journal of Mircorbiological Methods, Elsevier, Amsterdam, NL, vol. 41, No. 2 Jul. 1, 2000, pp. 85-112.
Moter A et al: "Fluorescence in Situ Hybridization Shows Spatial Distribution of Asyet Uncultured Treponemes in Biopsies From Digital Dermatitis Lesions", Microbiology, Society for General Microbioolgy, GB, vol. 144, no. Part 09, Jan. 1, 1998, pp. 2459-2467.

*Primary Examiner* — James Martinell
(74) *Attorney, Agent, or Firm* — JMB Davis Ben-David

(57) ABSTRACT

The invention relates to a control preparation (e.g. comprising microorganism control cells embedded in a cold polymerising resin or plastic) for use in a method for detection of a target microorganism in microbiological pathology, comprising a plurality of section bodies joint by a joining polymer, wherein each section body comprises a matrix polymer (e.g. a cold polymerising resin or plastic). A first section body comprises a nucleic acid sequence specific for the target microorganism (e.g. microorganism cells used as positive control). A second section body comprises a second nucleic acid sequence, which in comparison to said first nucleic acid sequence, contains a deletion, an additional nucleoside or a different nucleoside in one, two, three or four positions of said second nucleic acid sequence and which does not hybridize to said first nucleic acid sequence under stringent conditions (e.g. cells from a related microorganism having 1-4 mismatches as compared to the target region of a FISH probe for the target microorganism). The invention further relates to methods for detection and discrimination of two microorganism species of the same genus in tissue sections, and to kits for use in this method.

12 Claims, 4 Drawing Sheets
Specification includes a Sequence Listing.

SEQUENCE LISTING

<160> NUMBER OF SEQ ID NOS: 46

<210> SEQ ID NO 1
<211> LENGTH: 18
<212> TYPE: RNA
<213> ORGANISM: Staphylococcus epidermidis

<400> SEQUENCE: 1
gcgcagagau auggagga                 18

<210> SEQ ID NO 2
<211> LENGTH: 18
<212> TYPE: RNA

```
<213> ORGANISM: Bacillus cereus

<400> SEQUENCE: 2
gcguagagau auggagga                                                   18

<210> SEQ ID NO 3
<211> LENGTH: 19
<212> TYPE: RNA
<213> ORGANISM: Staphylococcus aureus

<400> SEQUENCE: 3
cggacgagaa gcuugcuuc                                                  19

<210> SEQ ID NO 4
<211> LENGTH: 19
<212> TYPE: RNA
<213> ORGANISM: Staphylococcus lentus

<400> SEQUENCE: 4
cagaugagaa gcuugcuuc                                                  19

<210> SEQ ID NO 5
<211> LENGTH: 18
<212> TYPE: RNA
<213> ORGANISM: Enterococcus faecalis

<400> SEQUENCE: 5
cccaucagag ggggauaa                                                   18

<210> SEQ ID NO 6
<211> LENGTH: 18
<212> TYPE: RNA
<213> ORGANISM: Enterococcus faecium

<400> SEQUENCE: 6
cccaucagaa ggggauaa                                                   18

<210> SEQ ID NO 7
<211> LENGTH: 25
<212> TYPE: RNA
<213> ORGANISM: Enterococcus faecium

<400> SEQUENCE: 7
cauucaguug ggcacucuag caaga                                           25

<210> SEQ ID NO 8
<211> LENGTH: 25
<212> TYPE: RNA
<213> ORGANISM: Enterococcus faecalis

<400> SEQUENCE: 8
cauuuaguug ggcacucuag cgaga                                           25

<210> SEQ ID NO 9
<211> LENGTH: 18
<212> TYPE: RNA
<213> ORGANISM: Streptococcus pyogenes

<400> SEQUENCE: 9
gugcagaagg ggagagug                                                   18

<210> SEQ ID NO 10
<211> LENGTH: 18
```

```
<212> TYPE: RNA
<213> ORGANISM: Enterococcus faecalis

<400> SEQUENCE: 10
gugcagaaga ggagagug                                                 18

<210> SEQ ID NO 11
<211> LENGTH: 20
<212> TYPE: RNA
<213> ORGANISM: Tropheryma whippelii

<400> SEQUENCE: 11
ugguacagag gguugcaaua                                               20

<210> SEQ ID NO 12
<211> LENGTH: 20
<212> TYPE: RNA
<213> ORGANISM: Actinomyces odontolyticus

<400> SEQUENCE: 12
ugguacagag gguugcgaua                                               20

<210> SEQ ID NO 13
<211> LENGTH: 26
<212> TYPE: RNA
<213> ORGANISM: Candida albicans

<400> SEQUENCE: 13
gcaggccuuu gcucgaauau auuagc                                        26

<210> SEQ ID NO 14
<211> LENGTH: 26
<212> TYPE: RNA
<213> ORGANISM: Aspergillus fumigatus

<400> SEQUENCE: 14
gcaggccuuu gcucgaauac auuagc                                        26

<210> SEQ ID NO 15
<211> LENGTH: 22
<212> TYPE: RNA
<213> ORGANISM: Filifacor alocis

<400> SEQUENCE: 15
ucaaaacgau aguggacaaa ga                                            22

<210> SEQ ID NO 16
<211> LENGTH: 22
<212> TYPE: RNA
<213> ORGANISM: Filifactor villosus

<400> SEQUENCE: 16
ucaaagagaa aucggacaaa ga                                            22

<210> SEQ ID NO 17
<211> LENGTH: 24
<212> TYPE: RNA
<213> ORGANISM: Tannerella forsythia

<400> SEQUENCE: 17
uacaggggaa uaaaaugaga uacg                                          24

<210> SEQ ID NO 18
```

```
<211> LENGTH: 24
<212> TYPE: RNA
<213> ORGANISM: Porphyromonas gingivalis

<400> SEQUENCE: 18
uauacgggaa uaacgggcga uacg                                          24

<210> SEQ ID NO 19
<211> LENGTH: 24
<212> TYPE: RNA
<213> ORGANISM: Porphyromonas gingivalis

<400> SEQUENCE: 19
gaauaacggg cgauacgagu auug                                          24

<210> SEQ ID NO 20
<211> LENGTH: 24
<212> TYPE: RNA
<213> ORGANISM: Porphyromonas gulae

<400> SEQUENCE: 20
gaauaacggg cgauacgugu auug                                          24

<210> SEQ ID NO 21
<211> LENGTH: 29
<212> TYPE: RNA
<213> ORGANISM: Prevotella intermedia

<400> SEQUENCE: 21
uuguaaacug cuuuuguugg ggaguaaag                                     29

<210> SEQ ID NO 22
<211> LENGTH: 29
<212> TYPE: RNA
<213> ORGANISM: Prevotella byrantii B14

<400> SEQUENCE: 22
uuguaaacug cuuuuuuagg ggaauaaag                                     29

<210> SEQ ID NO 23
<211> LENGTH: 16
<212> TYPE: RNA
<213> ORGANISM: Aggregatibacter actinomycetemcomitans

<400> SEQUENCE: 23
gaaucugucu uaugga                                                   16

<210> SEQ ID NO 24
<211> LENGTH: 16
<212> TYPE: RNA
<213> ORGANISM: Haemophilus influenzae

<400> SEQUENCE: 24
gaaucuggcu uaugga                                                   16

<210> SEQ ID NO 25
<211> LENGTH: 21
<212> TYPE: RNA
<213> ORGANISM: Fusobacterium nucleatum

<400> SEQUENCE: 25
gagagcuuug cgucccauua g                                             21
```

```
<210> SEQ ID NO 26
<211> LENGTH: 21
<212> TYPE: RNA
<213> ORGANISM: Leptotrichia bucallis

<400> SEQUENCE: 26
gagagcuuug cguccauua g                                              21

<210> SEQ ID NO 27
<211> LENGTH: 18
<212> TYPE: DNA
<213> ORGANISM: Enterococcus faecalis

<400> SEQUENCE: 27
gggtagtctc cccctatt                                                 18

<210> SEQ ID NO 28
<211> LENGTH: 25
<212> TYPE: DNA
<213> ORGANISM: Enterococcus faecium

<400> SEQUENCE: 28
gtaagtcaac ccgtgagatc gttct                                         25

<210> SEQ ID NO 29
<211> LENGTH: 25
<212> TYPE: RNA
<213> ORGANISM: Enterococcus faecium

<400> SEQUENCE: 29
cauucaguug ggcacucuag caaga                                         25

<210> SEQ ID NO 30
<211> LENGTH: 25
<212> TYPE: RNA
<213> ORGANISM: Enterococcus faecalis

<400> SEQUENCE: 30
cauuuaguug ggcacucuag cgaga                                         25

<210> SEQ ID NO 31
<211> LENGTH: 18
<212> TYPE: DNA
<213> ORGANISM: Artificial Sequence
<220> FEATURE:
<223> OTHER INFORMATION: Probe sequence

<400> SEQUENCE: 31
gctgcctccc gtaggagt                                                 18

<210> SEQ ID NO 32
<211> LENGTH: 18
<212> TYPE: DNA
<213> ORGANISM: Artificial Sequence
<220> FEATURE:
<223> OTHER INFORMATION: Probe sequence

<400> SEQUENCE: 32
actcctacgg gaggcagc                                                 18

<210> SEQ ID NO 33
<211> LENGTH: 18
<212> TYPE: DNA
<213> ORGANISM: Artificial Sequence
<220> FEATURE:
```

```
<223> OTHER INFORMATION: Probe sequence

<400> SEQUENCE: 33
cgacggaggg catcctca                                                   18

<210> SEQ ID NO 34
<211> LENGTH: 18
<212> TYPE: DNA
<213> ORGANISM: Artificial Sequence
<220> FEATURE:
<223> OTHER INFORMATION: Probe sequence

<400> SEQUENCE: 34
tcctccatat ctctgcgc                                                   18

<210> SEQ ID NO 35
<211> LENGTH: 19
<212> TYPE: DNA
<213> ORGANISM: Artificial Sequence
<220> FEATURE:
<223> OTHER INFORMATION: Probe sequence

<400> SEQUENCE: 35
gaagcaagct tctcgtccg                                                  19

<210> SEQ ID NO 36
<211> LENGTH: 18
<212> TYPE: DNA
<213> ORGANISM: Artificial Sequence
<220> FEATURE:
<223> OTHER INFORMATION: Probe sequence

<400> SEQUENCE: 36
ttatccccct ctgatggg                                                   18

<210> SEQ ID NO 37
<211> LENGTH: 25
<212> TYPE: DNA
<213> ORGANISM: Artificial Sequence
<220> FEATURE:
<223> OTHER INFORMATION: Probe sequence

<400> SEQUENCE: 37
tcttgctaga gtgcccaact gaatg                                           25

<210> SEQ ID NO 38
<211> LENGTH: 18
<212> TYPE: DNA
<213> ORGANISM: Artificial Sequence
<220> FEATURE:
<223> OTHER INFORMATION: Probe sequence

<400> SEQUENCE: 38
cactctcccc tyctgcac                                                   18

<210> SEQ ID NO 39
<211> LENGTH: 20
<212> TYPE: DNA
<213> ORGANISM: Artificial Sequence
<220> FEATURE:
<223> OTHER INFORMATION: Probe sequence

<400> SEQUENCE: 39
tattgcaacc ctctgtacca                                                 20
```

```
<210> SEQ ID NO 40
<211> LENGTH: 26
<212> TYPE: DNA
<213> ORGANISM: Artificial Sequence
<220> FEATURE:
<223> OTHER INFORMATION: Probe sequence

<400> SEQUENCE: 40
gctaatatat tcgagcaaag gcctgc                                      26

<210> SEQ ID NO 41
<211> LENGTH: 22
<212> TYPE: DNA
<213> ORGANISM: Artificial Sequence
<220> FEATURE:
<223> OTHER INFORMATION: Probe sequence

<400> SEQUENCE: 41
tctttgtcca ctatcgtttt ga                                          22

<210> SEQ ID NO 42
<211> LENGTH: 24
<212> TYPE: DNA
<213> ORGANISM: Artificial Sequence
<220> FEATURE:
<223> OTHER INFORMATION: Probe sequence

<400> SEQUENCE: 42
cgtatctcat tttattcccc tgta                                        24

<210> SEQ ID NO 43
<211> LENGTH: 24
<212> TYPE: DNA
<213> ORGANISM: Artificial Sequence
<220> FEATURE:
<223> OTHER INFORMATION: Probe sequence

<400> SEQUENCE: 43
caatactcgt atcgcccgtt attc                                        24

<210> SEQ ID NO 44
<211> LENGTH: 29
<212> TYPE: DNA
<213> ORGANISM: Artificial Sequence
<220> FEATURE:
<223> OTHER INFORMATION: Probe sequence

<400> SEQUENCE: 44
ctttactccc caacaaaagc agtttacaa                                   29

<210> SEQ ID NO 45
<211> LENGTH: 16
<212> TYPE: DNA
<213> ORGANISM: Artificial Sequence
<220> FEATURE:
<223> OTHER INFORMATION: Probe sequence

<400> SEQUENCE: 45
tccataagac agattc                                                 16

<210> SEQ ID NO 46
<211> LENGTH: 21
<212> TYPE: DNA
<213> ORGANISM: Artificial Sequence
<220> FEATURE:
<223> OTHER INFORMATION: Probe sequence
```

-continued

```
<400> SEQUENCE: 46
ctaatgggac gcaaagctct c                                              21
```

CONTROL PREPARATION FOR FISH METHODS IN MICROBIOLOGY

CROSS-REFERENCE TO RELATED APPLICATIONS

This is the U.S. National Stage of International Application No. PCT/EP2016/051630 filed on Jan. 27, 2016, which was published in English under PCT Article 21(2), which in turn claims the benefit of German Patent Application No. 10 2015 101 168.9 filed on Jan. 27, 2015.

The invention relates to a control preparation comprising target sequences for fluorescence in situ hybridization (FISH) probes encased in a polymer body, and to methods for use of these control preparations in microbiological pathology.

BACKGROUND

Bacterial infections are among the ten most frequent causes of death. A fast diagnosis and initiation of a targeted therapy contribute significantly to reducing the mortality of infections, which in many cases start in biofilms, sedentary associations of microorganisms in and on the body. Gene expression in biofilms is clearly different from that of planktonic or freely submersed cells.

Biofilms contribute to numerous clinical pictures in the realm of infections, both as mono-species biofilms (endocarditis, infections of implants or catheters) or multi-species biofilms (oral biofilms, chronic wounds, otitis media). This life form offers microorganisms important advantages, such as inner-biofilm food chains, increased recalcitrance against antibacterial drugs and protection from immune mechanisms. While biofilms have been studies extensively in vitro, our knowledge about medically relevant biofilms in vivo is limited, as models fail to accurately depict the complex ecological conditions of the human body. No methods are available in routine diagnostic to detect and analyse biofilms.

Fluorescence in situ hybridization (FISH) is a method of molecular biology that allows for the visualization and identification of a microorganism, irrespective of having cultured the microorganism. The principle of FISH is based on oligonucleotide probes coupled to a fluorescent dye. These probes bind, in dependency of the sequence match, to bacterial sequences, for example the bacterial ribosomal RNA. Thus, bacteria can not only be visualized in their natural habitat, but also identified by species or strain. Combining different specific probes having different fluorescent tags allows for simultaneously showing several populations at once (Multiplex-FISH). FISH of tissue sections was established by embedding tissue samples in synthetic resin. This allows for analysing the number, spatial distribution and bacterium-host interactions even of bacteria that can not be cultured, in their natural habitat. FISH is an ideal instrument for the analysis of biofilms and infections in situ.

Suitable probe panels can help diagnosing infections through FISH. Protocols for fixating, embedding and hybridization are needed and must be adjusted to each other in order to achieve optimal results.

Since specificity of the oligonucleotide probes is an indispensable requirement for using FISH for diagnostic purposes, and in some applications, sequences having only one mismatch at the site of probe recognition must be discerned, adequate positive and negative controls need to be performed for each hybridization.

Such controls are usually fixated in fixation solution, and are stored subsequently at −20° C. This process however impedes the proliferation of standardized commercial control preparations having the quality that is necessary for routine application.

Currently, the user needs to keep the necessary control strains in culture. This is difficult to realize for users in clinical pathology, particularly if the controls concern hard to culture oral flora that grow slowly (anaerobic organisms), which even well equipped microbiological laboratories find impossible to keep in routine stock. Furthermore, the rRNA content of the control strains used is often not controlled or standardized due to different conditions of culture, which can make interpretation of results achieved by different laboratories very difficult.

Furthermore, control preparations prepared ad-hoc have a short shelf life due to the instability of RNA and need to be generated repeatedly, which again impacts the reproducibility of results. Another disadvantage is that when shipping such control preparations, the cold chain needs to be maintained.

Departing from the above state of the art, the objective of the instant invention is to provide means and methods for facilitating routine FISH analysis by adequate control preparations. This objective is attained by the subject matter of the independent claims.

According to a first aspect of the invention, a control preparation for use in a method for detection of a target microorganism in microbiological pathology is provided. The control preparation of the invention is characterized in that it comprises a plurality of section bodies, wherein the section bodies are joint by a joining polymer, and wherein each section body comprises a matrix polymer, and wherein a. a first section body comprises a first nucleic acid sequence, which is 100% identical to a nucleic acid sequence comprised in the target microorganism;

b. a second section body comprises a second nucleic acid sequence, which in comparison to said first nucleic acid sequence, contains a deletion, an additional nucleotide or a different nucleotide in one, two, three or four positions of said second nucleic acid sequence.

The first nucleic acid sequence is thus 100% reverse complementary to a nucleic acid sequence, that can be used for detection of the target microorganism (such as a FISH probe), and will bind under stringent conditions to such FISH probe, while a probe nearly identical in sequence, i.e. one that differs in one, two, three or four positions would not bind.

A second section body similarly disposed within the control preparation comprises a second nucleic acid sequence, which is almost, but not 100% identical with a nucleic acid sequence of the target microorganism. Typically, the difference to the reverse complementary nucleic acid sequence of the target microorganism (i.e., to the first nucleic acid sequence of the first section body) is one, two, three or four positions, in which the second nucleic acid sequence shows a deletion, an additional or a different nucleotide. The second nucleic acid sequence is thus reverse complementary identical in one, two, three or four positions to a nucleic acid sequence that can be used for detection of the target microorganism (such as the FISH probe mentioned above).

The first section body thus serves as a "positive control" while the second section body serves as a negative control or specificity control. The probe employed in this context, which is specific for a DNA or RNA sequence occurring in the target microorganism, should show binding to the first section body, but not to the second (or else the binding conditions would be nonspecific).

In the present specification, nucleic acid sequences are given in the direction of 5' (left end) to 3' (right end) according to the convention of biology. If a sequence A is designated "reverse complementary" to a sequence B, A and B can hybridize in perfect fashion, i.e. each position of A, counted from the 5' end, corresponds to a perfectly matched (A matches T or U and G matches C) position of B counted from the 3' end.

Examples of reverse complementary sequences are ATC and GAT. The sequence directly (not reverse!) complementary to ATC is TAG.

Identity in the context of the present specification is a single quantitative parameter representing the result of a sequence comparison (Alignment) position by position as a quantitative result (percent identity). Methods of sequence comparison are known in the art; the BLAST algorithm available publicly is an example. One example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear.

Unless otherwise stated, identity values given in the present specification refer to values obtained with the BLAST programme package using default parameters (Altschul et al., J. Mol. Biol. 215:403-410 (1990)). This programme is publicly available (http://blast.ncbi.nlm.nih.gov/).

In certain embodiments, the first and the second nucleic acid sequence each independently of the other have a length of approximately 12 to 30 nucleotides. In certain embodiments, the first and the second nucleic acid sequence each independently of the other are comprised within a longer sequence.

In certain embodiments, the first and the second nucleic acid sequence, or the probes used in the methods of the invention as disclosed herein, each independently of any other are DNA or RNA oligonucleotides or RNA analogues (such as 2'-O-methyl-RNA; LNA ("locked" nucleic acids, in which the 2'-O and the 4'-C are bridged by a covalent linkage); PNA ("peptide nucleic acids", nucleobases linked by a peptide chain); BNA (ribose analogues bridged by a amino ethylene moiety between the 2'-O and the 4'-C); morpholino RNA and equivalents of these building blocks known to the skilled artisan, and mixtures thereof).

In certain embodiments, the first and the second nucleic acid sequence each independently of the other are an RNA sequence.

In certain embodiments, the first nucleic acid sequence a RNA sequence specific for the target microorganism, typically a 16S rRNA-, 23S rRNA-, 18S rRNA-, ISR (intergenic spacer region) or mRNA sequence or a part thereof.

In certain embodiments, the first and the second nucleic acid sequence each independently of the other are part of a 16S, 23S, 18S or ISR-RNA sequence.

In certain embodiments, the first and the second nucleic acid sequence each independently of the other is provided on particles or compartments, particularly cells, having a size of 0.1 μm to 30 μm. This leads to fluorescence signals generated by hybridization of a FISH probe are concentrated in space and thus easier to detect. In certain embodiments, the compartments are cells, particularly cells of the target microorganism. i.e. cells that comprise the first or second nucleic acid sequence as part of their genetic makeup, for example as ribosomal RNA.

In certain embodiments, each section body comprises a plurality of individuals of exactly one microorganism embedded in the matrix polymer, with each section body having individuals of a different microorganism, wherein said first nucleic acid sequence is comprised in the microorganism of said first section body and said second nucleic acid sequence is comprised in said microorganism of said second section body.

In certain particular embodiments, the nucleic acid sequence are part of a microorganism embedded in the matrix polymer, for examples as ribosomal RNA of the microorganism. Even more particularly, the first (NAS1) and second nucleic acid sequence (NAS2) is taken from the following table:

TABLE 1

| probe used in detection of: | | Control species target sequence 5' - 3 | Sequence ID; Accession No. | Species |
|---|---|---|---|---|
| Staphylococcus spp. | NAS 1 | GCGCAGAGAUAUGGAG GA | SEQ ID NO 001 AE 15929 | Staphylococcus epidermidis |
| | NAS 2 | GCGUAGAGAUAUGGAG GA | SEQ ID NO 002 AF290547 | Bacillus cereus |
| S. aureus | NAS 1 | CGGACGAGAAGCUUGC UUC | SEQ ID NO 003 AASB02000198 | Staphylococcus aureus subsp. aureus |
| | NAS 2 | CAGAUGAGAAGCUUGC UUC | SEQ ID NO 004 ATCC 29070 | Staphylococcus lentus |
| E. faecalis | NAS 1 | CCCAUCAGAGGGGAU AA | SEQ ID NO 005 NZ_CP008816 | Enterococcus faecalis |
| | NAS 2 | CCCAUCAGAAGGGGAU AA | SEQ ID NO 006 NR_115764 | Enterococcus faecium |
| E. faecium | NAS 1 | CAUUCAGUUGGGCACU CUAGCAAGA | SEQ ID NO 007 NR_115764 | Enterococcus faecium |
| | NAS 2 | CAUUUAGUUGGGCACU CUAGCGAGA | SEQ ID NO 008 NZ_CP008816 | Enterococcus faecalis |
| Streptococcus spp. | NAS 1 | GUGCAGAAGGGGAGAG UG | SEQ ID NO 009 CP008926.1 | Streptococcus pyogenes |
| | NAS 2 | GUGCAGAAGAGGAGAG UG | SEQ ID NO 010 NZ_CP008816 | Enterococcus faecalis |

TABLE 1-continued

| probe used in detection of: | | Control species target sequence 5' - 3 | Sequence ID; Accession No. | Species |
|---|---|---|---|---|
| Tropheryma whipplei | NAS 1 | UGGUACAGAGGGUUGC AAUA | SEQ ID NO 011 NC_004572 | Tropheryma whipplei |
| | NAS 2 | UGGUACAGAGGGUUGC GAUA | SEQ ID NO 012 X80504 | Actinomyces odontolyticus |
| Candida spp. | NAS 1 | GCAGGCCUUUGCUCGA AUAUAUUAGC | SEQ ID NO 013 HQ876034 | Candida albicans |
| | NAS 2 | GCAGGCCUUUGCUCGA AUACAUUAGC | SEQ ID NO 014 AF548061 | Aspergillus fumigatus |
| Filifactor alocis | NAS 1 | UCAAAACGAUAGUGGA CAAAGA | SEQ ID NO 015 CP002390 | Filifactor alocis |
| | NAS 2 | UCAAAGAGAAAUCGGA CAAAGA | SEQ ID NO 016 F537211 | Filifactor villosus |
| Tannerella forsythia | NAS 1 | UACAGGGGAAUAAAAU GAGAUACG | SEQ ID NO 017 | Tannerella forsythia |
| | NAS 2 | UAUACGGGAAUAACGG GCGAUACG | SEQ ID NO 018 NR_074234 | Porphyromonas gingivalis |
| Porphyromo- nas gingivalis | NAS 1 | GAAUAACGGGCGAUAC GAGUAUUG | SEQ ID NO 019 NR_074234 | Porphyromonas gingivalis |
| | NAS 2 | GAAUAACGGGCGAUAC GUGUAUUG | SEQ ID NO 020 AF208290 | Porphyromonas gulae |
| Prevotella intermedia | NAS 1 | UUGUAAACUGCUUUUG UUGGGGAGUAAAG | SEQ ID NO 021 | Prevotella intermedia |
| | NAS 2 | UUGUAAACUGCUUUUU UAGGGGAAUAAAG | SEQ ID NO 022 NR_028866 | Prevotella byrantii B14, |
| Aggregatibac- ter actinomyce- temcomitans | NAS 1 | GAAUCUGUCUUAUGGA | SEQ ID NO 023 AY362884 | Aggregatibacter actinomyce- temcomitans |
| | NAS 2 | GAAUCUGGCUUAUGGA | SEQ ID NO 024 M35019 | Haemophilus influenzae |
| Fusobac- terium spp. | NAS 1 | GAGAGCUUUGCGUCCC AUUAG | SEQ ID NO 025 AB573068 | Fusobacterium nucleatum subsp. nucleatum |
| | NAS 2 | GAGAGCUUUGCGUCCU AUUAG | SEQ ID NO 026 CP001685 | Leptotrichia buccalis |

In certain embodiments, the joining polymer and the matrix polymer comprise a common monomer unit. This enhances the chemical union of the two components and facilitates microtome sectioning of the compound as a single preparation.

In certain embodiments, the joining polymer and the matrix polymer are made of essentially the same monomer units. In certain embodiments, the joining polymer and the matrix polymer comprise, or essentially are made of, polymethacrylic acid alkyl esters, particularly polymethylmetacrylate. This polymer is well known in histology and can be used by trained staff without further instructions for making section preparations. It is well suited for employment of FISH probes.

In certain embodiments, the control preparation is positioned on a microscopic sample holder and each section body is positioned within the control preparation so that the identity of the section body can be identified unambiguously by its position relative to
  a. a shape of the control preparation;
  b. a shape of said sample holder and/or
  c. a reference point or reference body disposed on said sample holder.

This arrangement allows avoiding mistakes in positioning the control preparation, which could ultimately lead to an erroneous attribution of the measurement being made. In certain embodiments, the control preparation is shaped as a cuboid tapering or thinning on one side to facilitate cutting on the microtome.

In embodiments where a reference body is present, this can be used for orientation of the control preparation, but also as a reference of fluorescence intensity, which depends on the microscope (e.g. quality of the light source, correct beam path). Thus, the reference body can be used as an internal validation and quality control of the fluorescence signal for the positive and negative controls. The control body is a symmetrical or asymmetrical form and of a stable, standardized autofluorescence in a given fluorescence channel.

According to a second aspect of the invention, a method for detection of a target microorganism in a tissue preparation is provided. This method comprises the following steps:
  a. The tissue preparation is contacted with a fluorescently labelled oligonucleotide probe. Said oligonucleotide probe is specific for the target microorganism under conditions that allow binding of the oligonucleotide probe to a target sequence, wherein said target sequence is 100% reverse complementary to said probe, and wherein said conditions will inhibit binding of said oligonucleotide probe to a sequence that is different in one to four positions to said target sequence (its reverse complementary sequence);

b. In another step, said fluorescently labelled oligonucleotide probe used in the preceding step a is contacted with a control preparation according to the first aspect of the invention or any of its embodiments to achieve a positive control. The first nucleic acid sequence of the first section body of the control preparation is 100% reverse complementary identical to the sequence of said fluorescently labelled oligonucleotide probe, i.e. the oligonucleotide probe hybridizes perfectly to the nucleic acid of the target organism and the positive control. The second nucleic acid sequence of said second section body is different in comparison to said first nucleic acid sequence, in that it contains a deletion, an additional nucleoside or a different nucleoside in one, two, three or four positions of said second nucleic acid sequence. Thus, it does not match perfectly and will not show a binding of the oligonucleotide probe to the second section body under conditions that require 100% match (negative or specificity control).

c. Subsequently, the results of steps a and b are analysed optically either by inspection or automated image analysis. If the fluorescently oligonucleotide probe has bound to the target sequence in step a, and the fluorescently oligonucleotide probe likewise has bound to the first nucleic acid sequence of the first section body in step b, but has not bound to the second nucleic acid sequence of the second section body in step b, the interpretation is that the target microorganism is present in the sample.

Different species or genera of microorganisms may be detected using oligonucleotide probes, labelled with different fluorescent dyes, or combination of different dyes.

In certain embodiments, any one of the following fluorescent dyes are employed: FITC, cyanin 3, TAMRA, Texas red and cyanin 5, or derivatives of these dyes. In certain embodiments, FITC, cyanin 3 and cyanin 5 are employed. Depending on the equipment of the microscope with fitting filter sets, 2 or 3 oligonucleotide probes may be combined, optionally together with the nucleic acid dye DAPI. Confocal microscopy and the analysis of spectra allow detecting more than a dozen of different dyes or combinations thereof.

In certain embodiments, the analysis of the method is performed automatically.

In certain embodiments, a first and a second target microorganism of different species having the same genus are detected or discriminated in a tissue preparation. Therein, a first, second ($3^{rd}$, $4^{th}$ ... )fluorescently labelled oligonucleotide probe is used that is specific for each first and second (and $3^{rd}$, $4^{th}$ ... where applicable) microorganism. Ideally, the control preparation provides a positive control and a negative control for each pair of microorganisms in such fashion that two closely related but genetically distinct pathogens can serve to complement each other's positive and negative control. Thus, a first oligonucleotide probe is used, which is specific for the first target microorganism, and which is 100% reverse complementary identical to the first nucleic acid sequence of said first section body, and a second oligonucleotide probe is used, which is specific for the second target microorganism, and which is 100% reverse complementary identical to the second nucleic acid sequence of said second section body.

Particular embodiments of the invention make use of the following sequence pairs:

TABLE 2

Example:

| First probe: detection of *Enterococcus faecalis* | |
|---|---|
| *E. faecalis* specific probe | 3'- GGG TAG TCT CCC CCT ATT-5' Probe S6 (SEQ ID NO 027) |
| rRNA sequence of *E. faecalis* | 5'-CCC AUC AGA GGG GGA UAA-3' positive control (SEQ ID NO 005) |
| rRNA sequence of *E. faecium* | 5'-CCC AUC AGA AGG GGA UAA-3' negative control (SEQ ID NO 006) |
| Second probe: detection of *Enterococcus faecium* | |
| *E. faecium*-spez. Probe | 3'- GTA AGT CAA CCC GTG AGA TCG TTC T-5' Probe S7 (SEQ ID NO 028) |
| *E. faecium* rRNA Seq. | 5'-CAU UCA GUU GGG CAC UCU AGC AAG A-3' positive control (SEQ ID NO 029) |
| *E. faecalis* rRNA Seq. | 5'-CAU UUA GUU GGG CAC UCU AGC GAG A-3' negative control (SEQ ID NO 030) |

The reverse complementary sequences of the preceding sample sequences are employed as first and second nucleic acid sequence of the control preparation. In particular embodiments, the sequences are provided as part of the 16S RNA comprised within said species, wherein cells of the species are embedded and fixed within said control preparation.

In certain embodiments, the sequences named in a and b are comprised as part of a bacterial RNA. In certain embodiments, the sequences named in a and b are DNA or DNA analogues, in which case the positions designated as U (uracil) may be T (thymidine).

In certain embodiments, the probe named in c. is a DNA oligomer or an oligomer comprising or consisting of DNA analogues.

According to a third aspect of the invention, a kit for use in a method for detection of a target microorganism in a tissue preparation is provided. This kit comprises the following components:

a. A fluorescently labelled oligonucleotide probe as specified under the above aspects and embodiments of the invention. The oligonucleotide probe is specific for the target microorganism under conditions that allow binding of the oligonucleotide probe to a target sequence that is 100% reverse complementary to said probe, and wherein said conditions will inhibit binding of said oligonucleotide probe to a sequence that is different in one, two, three or four positions to said target sequence. In other words, this fluorescently labelled oligonucleotide probe is a FISH probe employable for specific detection of the target organism having a length of 12 to 30 nucleotides and being 100% reverse complementary to the first nucleic acid sequence of the control preparation.

b. A fluorescently labelled nonsense oligonucleotide probe, which does not bind to the RNA or DNA of any known microorganism under the conditions identified in paragraph a. This nonsense probe serves the purpose of controlling whether the conditions or the nature of the preparation/sample favour an unspecific binding of nucleic acids to the preparation. In certain embodiments, controls are used that show a similar or identical base composition compared to the specific oligonucleotide probe (para a). Such composition can be achieved by using the sequence complementary (not reverse complementary) to the specific probe. For a probe sequence ATG, this would be TAC (the probes of the invention are longer, but the principle of base composition is demonstrated with this short sequence).

c. A control preparation according to the first aspect of the invention or any of its embodiments mentioned herein. This comprises a first nucleic acid sequence of the first section body, which hybridizes to said fluorescently labelled oligonucleotide probe under the conditions identified in paragraph a (i.e., is 100% reverse complementary identical), and a second nucleic acid sequence of said second section body, which does not hybridize to said fluorescently labelled oligonucleotide probe under the conditions identified in paragraph a.

d. Optionally, the kit further comprises more components. Of special mention are:
   i. A fluorescent dye binding to polynucleotides in an unspecific fashion, particularly 4',6-diamidino-2-phenylindol (DAPI).
   ii. A fluorescently labelled oligonucleotide probe binding to a 16S-RNA consensus sequence that is comprised in the great majority of bacteria (a so-called "panbacterial probe") and serves to detect the presence of bacteria without further specificity of species or genus.
   iii. A fluorescently labelled oligonucleotide probe binding to a 16S-RNA consensus sequence that is comprised in all species of a genus and serves to detect the presence of bacteria of a particular genus without species specificity;
   iv. A fluorescently labelled oligonucleotide having no target in currently known bacteria (nonsense probe), which serves to identify unspecific binding.

In certain embodiments, the kit is designed for use in a method for detecting and discriminating a first and a second target microorganism of different species, but of the same genus, or of different genera or bacterial groups, in a tissue preparation. It comprises a fluorescently labelled first oligonucleotide probe ("first probe"), wherein said first oligonucleotide probe is specific for said first target microorganism under conditions that allow binding of the oligonucleotide probe to a target sequence, wherein said target sequence is 100% reverse complementary to said oligonucleotide probe, and wherein said conditions will inhibit binding of said oligonucleotide probe to a sequence that is different in one, two, three or four positions to said target sequence. Furthermore, it comprises a fluorescently labelled second oligonucleotide probe ("second probe"), wherein said second oligonucleotide probe is specific for said second target microorganism under the conditions identified above (paragraph a. i.).

Optionally, a fluorescently labelled nonsense oligonucleotide probe, which does not bind to the RNA or DNA of a known microorganism under the conditions identified above is also contained within the kit. A panbacterial probe may also be comprised as part of the kit.

Furthermore, the kit comprises a control preparation according to according to any one of the aspects or embodiments disclosed herein, wherein the control preparation comprises:
   i. A first nucleic acid sequence of the first section body that hybridizes to the first oligonucleotide probe under the conditions identified in paragraph a. above and that does not hybridize to said fluorescently labelled second oligonucleotide probe under such conditions.
   ii. A second nucleic acid sequence of the second section body, which does not hybridize to the first oligonucleotide probe but with the second oligonucleotide probe under such conditions.

In certain embodiments a combination of reagents for practicing the method of the invention (kit) comprises the following sequences:
   a. A first nucleic acid sequence comprising a sequence designated NAS 1 in table 1 (positive control)
   b. a second nucleic acid sequence comprising a sequence designated as NAS 2 in table 1 and associated (same line) to the sequence designated as NAS 1 in the preceding paragraph (negative or specificity control)
   c. a fluorescently labelled oligonucleotide probe that is completely reverse complementary to the first nucleic acid sequence named in paragraph a.

In certain embodiments a combination of reagents for practicing the method of the invention (kit) comprises the following sequences:
   a. a fluorescently labelled oligonucleotide probe;
   b. a first nucleic acid sequence (positive control)
   c. a second nucleic acid sequence (negative/specificity control)
   d. a probe specific for eubacteria (S1)
   e. genus specific probes (S4, S8, S10, S16, S17 and/or S18)
   f. species specific probes (S5, S6, S7, S9, S11, S12, S13, S14 and/or S15)

The control preparations and FISH kits of the present invention allow routine detection and visualization of biofilms and microorganisms in tissues and on medical devices by microscope for the first time. The pathogens associated with an infection can thus by identified quickly, which allows starting therapy early and specifically.

Advantages of the invention with view to the state of the art are, inter alia, that the control preparations may be supplied commercially as object holders having the standard dimensions of microscopy as a kit having a composition designed to optimally suit the application at hand. The control preparations do not require refrigeration, are insensitive to temperature changes and can be stored for at least three years. Laborious cultivation of control strains by the user can thus be avoided. Another advantage is the constant quality of the control preparations, achieved by invariant ribosomal content of the bacteria, and an internal option for validating the fluorescence intensity through the reference body.

On the level of process management, the control preparations of the invention allow controlling of the signal intensity in FISH and avoid making the result of the process dependent on the proficiency level of the person performing the process. They further provide for a more efficient use of reagents, as in one section, several bacterial species may be hybridized in one step. This further leads to time savings upon analysis of the experiment, i.e. at the microscope, as all controls are placed within one slide. Automation of the hybridization and analysis process is also facilitated.

the recommendation of a specific antibacterial regime during or after cardiac valve or prosthesis operations.

The FISH probe panel of the example detects 95% of typical endocarditis pathogens even in heart valves and prosthesis negative in culture, according to current ESC guidelines (staphylococci, streptococci, enterococci and *Candida*).

TABLE 3 cardiac kit sequences

| Seq. ID NO | Sequence 5' - 3' | Target species |
|---|---|---|
| S1 SEQ ID NO 31 | GCT GCC TCC CGT AGG AGT | 16S rRNA of most microorganisms of the bacteria domain |
| S2 SEQ ID NO 32 | ACT CCT ACG GGA GGC AGC | No rRNA of most microorganisms of the bacteria domain, but of the 16S rRNA gene |
| S3 SEQ ID NO 33 | CGA CGG AGG GCA TCC TCA | Nonsense sequence, no target |
| S4 SEQ ID NO 34 | TCC TCC ATA TCT CTG CGC | *Staphylococcus* spp. |
| S5 SEQ ID NO 35 | GAA GCA AGC TTC TCG TCC G | *Staphylococcus aureus* |
| S6 SEQ ID NO 36 | TTA TCC CCC TCT GAT GGG | *Enterococcus faecalis, E. sulfureus, Granulicatella* spp. |
| S7 SEQ ID NO 37 | TCT TGC TAG AGT GCC CAA CTG AAT G | *E. faecium, E. durans, Lactobacillus buchneri* |
| S8 SEQ ID NO 38 | CAC TCT CCC CTY CTG CAC | *Streptococcus* spp. |
| S9 SEQ ID NO 39 | TATTGCAACCCTCTGTACCA | *Tropheryma whipplei* |
| S10 SEQ ID NO 40 | GCT AAT ATA TTC GAG CAA AGG CCT GC | *Candida* spp. |

The control preparations of the invention help to avoid user errors at the microscope by facilitating an unambiguous association of bacterial species through the asymmetrical section (avoids confusion when pipetting).

The invention is further illustrated by the following examples and figures, which are meant to illustrate but not limit the invention:

EXAMPLES

Exemplary FISH Kits for diagnosis of endocarditis and peri-implantitis are shown.

Cardiac Kit

The exemplary "cardiac kit" facilitates the diagnosis of life-threatening cardiac infections, such as endocarditis, and In certain embodiments, the following combinations of two or three probes are employed:

TABLE 4 cardiac kit composition

| | Sequence ID | 5'-fluorescent dye | For detection of |
|---|---|---|---|
| Cardio Mix 1 | S1 | Cy3 | bacteria |
| | S3 | FITC | |
| Cardio Mix 2 | S6 | Cy3 | *Enterococcus faecalis* |
| | S7 | FITC | *Enterococcus faecium* |
| Cardio Mix 3 | S4 | Cy3 | *Staphylococcus* spp. |
| | S8 | FITC | *Streptococcus* spp. |
| Cardio Mix 4 | S9 | Cy3 | *Tropheryma whipplei* |
| | S10 | FITC | *Candida* spp. |
| Cardio Mix 5 | S5 | Cy3 | *Staphylococcus aureus* |
| | S4 | FITC | *Staphylococcus* spp. |
| Cardio Mix 6 | S4 | Cy3 | *Staphylococcus* spp. |
| | S8 | FITC | *Streptococcus* spp. |
| | S1 | Cy5 | bacteria |
| Cardio Mix 7 | S6 | Cy3 | *Enterococcus faecalis* |
| | S7 | FITC | *Enterococcus faecium* |
| | S1 | Cy5 | bacteria |
| Cardio Mix 8 | S1 | Cy3 | bacteria |
| | S10 | FITC | *Candida* spp. |
| | S3 | Cy5 | |

TABLE 4-continued cardiac kit composition

| | Sequence ID | 5'-fluorescent dye | For detection of |
|---|---|---|---|
| Cardio Mix 9 | S5 | Cy3 | *Staphylococcus aureus* |
| | S4 | FITC | *Staphylococcus* spp. |
| | S1 | Cy5 | bacteria |

Figure 1:
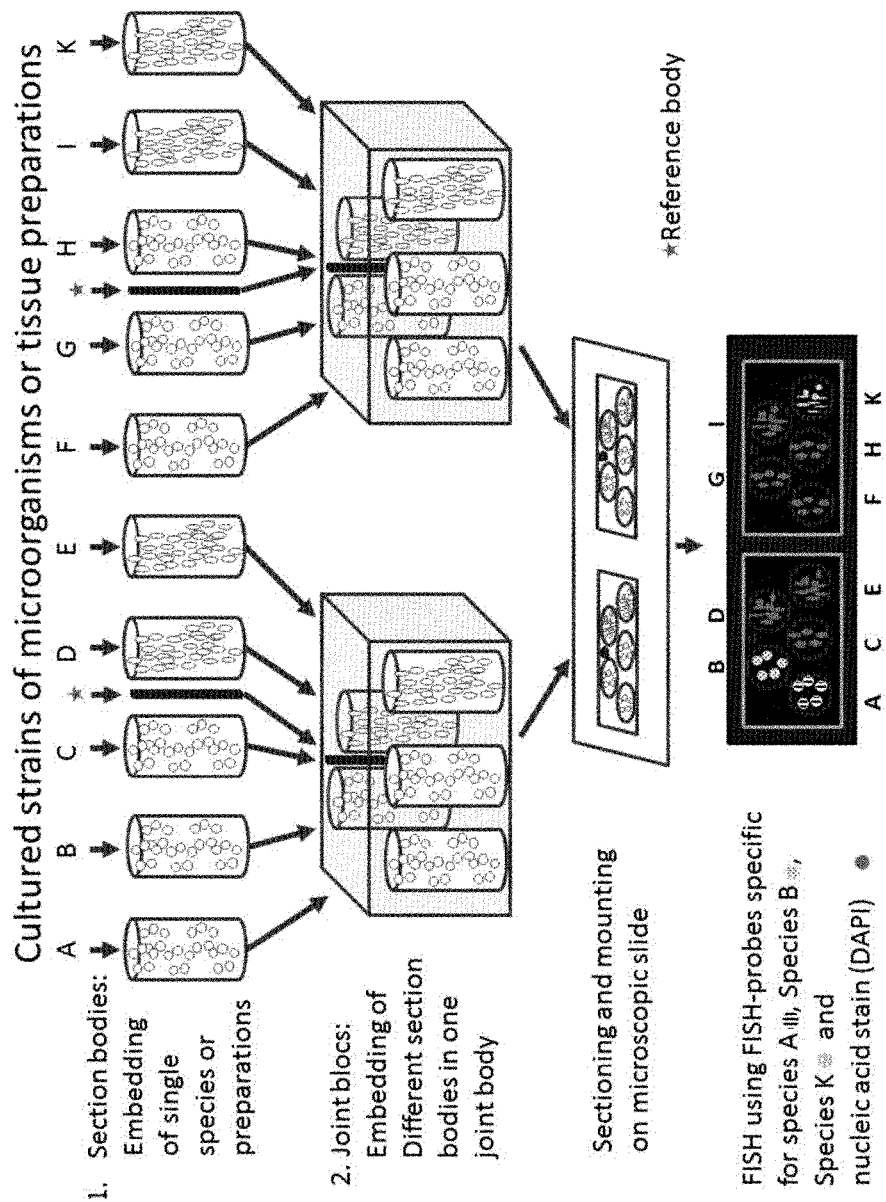
FIG. 1 shows the setup of the control preparation schematically.
Figure 2:
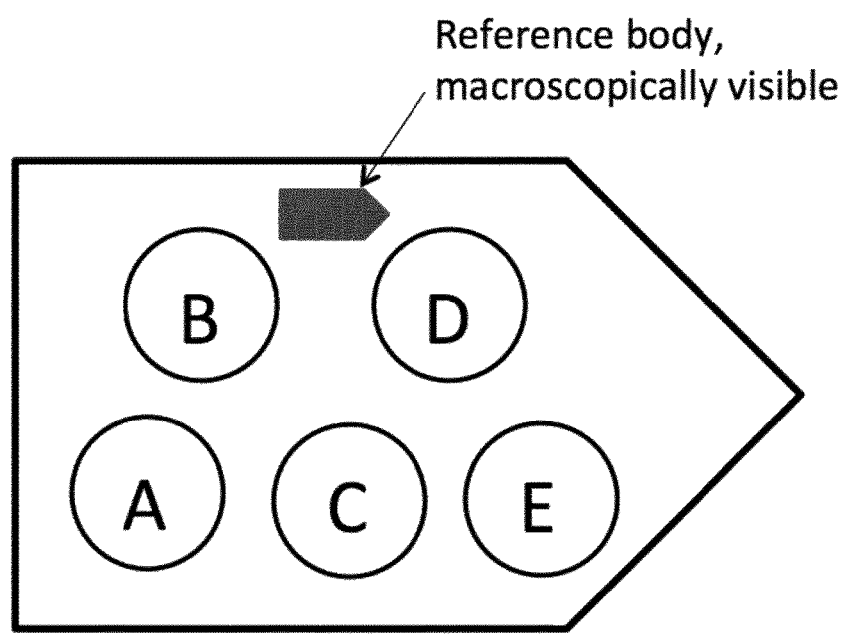
FIG. 2 shows the top view onto a section of the control preparation schematically.
Figure 3:
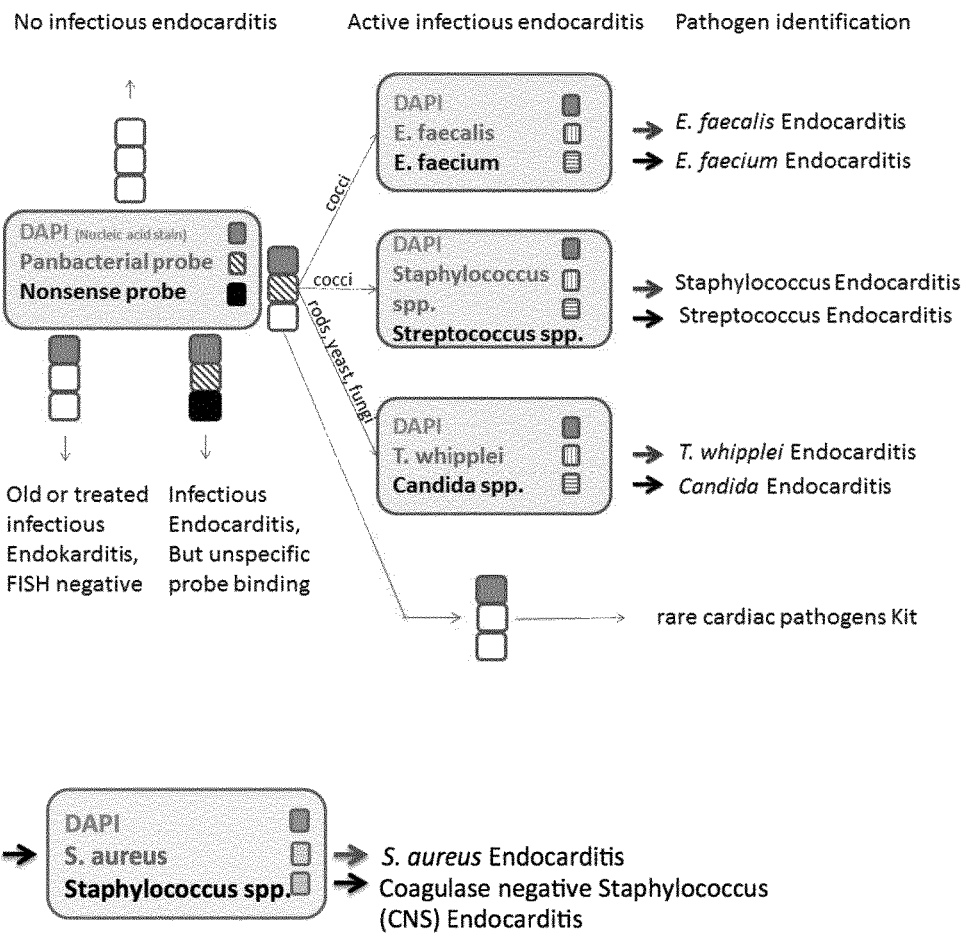
FIG. 3 shows an exemplary procedure for detecting microorganisms relevant in cardiology.

The concept behind the endocarditis kit for a microscope with filter sets for FITC, Cy3 and DAPI is shown schematically in FIG. 3.

Kit: Rare Cardiac Pathogens

Additionally, we have developed a FISH probe panel for rare pathogens of endocarditis, such as *Tropheryma whipplei, Bartonella* spp., *Propionibacterium* spp., *Lactobacillus* spp. and *Aerococcus* spp. A further component of the kits is the reagent for pulping the microorganisms and for tissue permeabilisation of the FISH probes. Both are requisites for successfully performing FISH on cardiac valves.

Oral Kit

The exemplary "oral kit" facilitates the identification of pathogens in periodontitis, a widespread disease, and in peri-implantitis (infection of dental implants).

The focus of the exemplary kits is in detection of pathogens of oral biofilms that are hard or impossible to keep in culture. The panel of probes for the typical causative agents of periodontitis is shown in the following table:

TABLE 5 probe sequences of the oral kit

| Seq. ID | Sequence 5' - 3' | Target Species |
|---|---|---|
| S1 SEQ ID NO 31 | GCT GCC TCC CGT AGG AGT | 16S rRNA of most microorganisms of the bacteria domain |
| S2 SEQ ID NO 32 | ACT CCT ACG GGA GGC AGC | No rRNA of most microorganisms of the bacteria domain, but of the 16S rRNA gene |
| S3 SEQ ID NO 33 | CGA CGG AGG GCA TCC TCA | Nonsense sequence, no target |
| S4 SEQ ID NO 34 | TCC TCC ATA TCT CTG CGC | *Staphylococcus* spp. |
| S10 SEQ ID NO 40 | GCT AAT ATA TTC GAG CAA AGG CCT GC | *Candida* spp. |
| S11 SEQ ID NO 41 | TCT TTG TCC ACT ATC GTT TTG A | *Filifactor alocis* |
| S12 SEQ ID NO 42 | CGT ATC TCA TTT TAT TCC CCT GTA | *Tannerella forsythia* |
| S13 SEQ ID NO 43 | CAA TAC TCG TAT CGC CCG TTA TTC | *Porphyromonas gingivalis* |
| S14 SEQ ID NO 44 | CTT TAC TCC CCA ACA AAA GCA GTT TAC AA | *Prevotella intermedial falsenii* |
| S15 SEQ ID NO 45 | TCC ATA AGA CAG ATT C | *Aggregatibacter actinomycetemcomitans* |
| S16 SEQ ID NO 46 | CTA ATG GGA CGC AAA GCT CTC | *Fusobacterium* spp. |

In certain embodiments, the following combinations are employed:

TABLE 6 composition of oral kit

| | Sequence ID | 5'-fluorescent dye | For detection of |
|---|---|---|---|
| Oral Mix 1 | S1 | Cy3 | bacteria |
| | S3 | FITC | — |
| Oral Mix 2 | S17 | Cy3 | *Actinomyces* spp. |
| | S10 | FITC | *Candida* spp. |
| Oral Mix 3 | S11 | Cy3 | *Filifactor alocis* |
| | S8 | FITC | *Streptococcus* spp. |
| Oral Mix 4 | S16 | Cy3 | *Fusobacterium* spp. |
| | S12 | FITC | *Tannerella forsythia*. |
| Oral Mix 5 | S13 | Cy3 | *Porphyromonas gingivalis* |
| | S14 | FITC | *Prevotella intermedia* |
| Oral Mix 6 | S15 | Cy3 | *Aggregatibacter actinomycetemcomitans* |
| | S18 | FITC | *Treponema* spp. |
| Oral Mix 7 | S1 | Cy3 | Bacteria |
| | S8 | FITC | *Streptococcus* spp. |
| | S3 | Cy5 | — |
| Oral Mix 8 | S17 | Cy3 | *Actinomyces* spp. |
| | S10 | FITC | *Candida* spp. |
| | S3 | Cy5 | — |
| Oral Mix 9 | S16 | Cy3 | *Fusobacterium* spp. |
| | S13 | FITC | *Porphyromonas gingivalis* |
| | S12 | Cy5 | *Tannerella forsythia*. |
| Oral Mix 10 | S11 | Cy3 | *Filifactor alocis* |
| | S4 | FITC | *Staphylococcus* spp. |
| | S1 | Cy5 | Bacteria |

TABLE 6-continued composition of oral kit

|  | Sequence ID | 5'-fluorescent dye | For detection of |
|---|---|---|---|
| Oral Mix 11 | S18 | Cy3 | *Treponema* spp. |
|  | S14 | FITC | *Prevotella intermedia* |
|  | S15 | Cy5 | *Aggregatibacter actinomycetemcomitans* |

The table in particular comprises pathogens that can be detected in periodontitis by means of PCR methods, and the of which is detection is established for dental practices. Examples are *Tannerella forsythia, Porphyromonas gingivalis, Prevotella intermedia, A. actinomycetemcomitans, Filifactor alocis* and *Treponema* spp. The pathologist or microbiologist can affirm the relative components and their spatial distribution within the biofilm. Additionally, the indicator pathogen can be identified and the therapeutic success can be assessed.

The oral kit can be applied both to histological tissue sections and to dental plaque. The kit detects classic periodontitis pathogens, but also *Candida* and Actinomycetes, which have a decisive role in therapy of peri-implantitis. Such mix also must contain a nonsense probe to facilitate an unambiguous interpretation of results. Probe binding properties, hybridization buffer and the fluorescence dye labels of the particular probes necessitate different probe combinations in a plurality of mixes.

Figure 4:
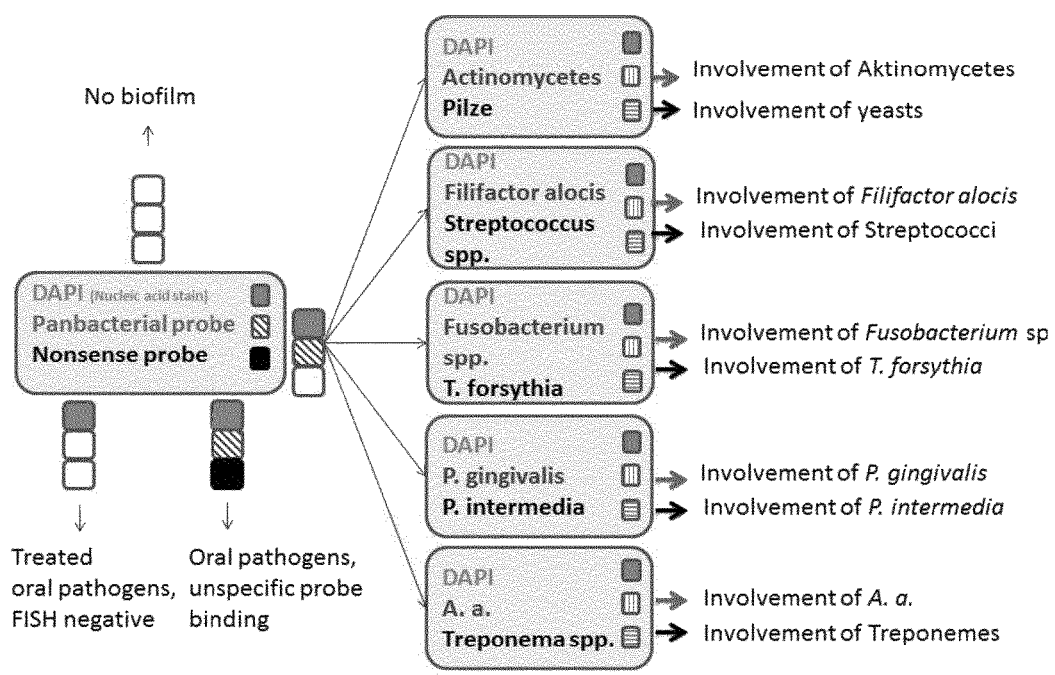
FIG. 4 shows an exemplary procedure for detecting microorganisms relevant for oral medicine.

The concept behind the oral kit for a microscope with filter sets for FITC, Cy3 and DAPI is shown schematically in FIG. 4.

Manufacture of the Control Preparations

In order to obtain the control preparations, the respective bacterial cultures are poured into synthetic resin and sections are made.

The synthetic resin is particularly suited for embedding because the hybridizations mix (including the FISH probes) can permeate the material unhindered, and the conditions for hybridization can be selected in a way to guarantee unimpeded association of probes to the bacterial RNA where a target sequence is present.

Several small blocks comprising bacterial species are made and combined into joint blocks, and sectioned, in order to save material, reagents and time. This facilitates the analysis of several controls per section.

Steps

Bacterial cultures are spun down during the exponential growth phase and are processed according to the embedding instructions of the Technovit 8100 technical manual (Heraeus Kulzer GmbH, 61273 Wehrheim). The bacterial pellet is kept during each change of solvent.

During the last step, the solution of methacrylate and the hardener are poured into small forms having an approx. size of 0.5×0.5×0.4 cm.

The hardened cylinders with bacteria inside are then jointly brought into a larger (approx. 1.0×0.8×0.4 cm) block, and are sectioned.

Workflow and Reagents

|  |  | T | duration |
|---|---|---|---|
| Fixation of material | Formaldehyde (37%) 1:10 in PBS pH 7.4 | 4° C. | 1 h-3 days according to sample size |
| Preparation of object holder | Dropwise application or application of tissue section |  |  |
| drying |  | 30° C. |  |
| dehydration | Only for samples applied dropwise: Increasing ethanol concentration 50%, 80%, 100% | RT | each 3 min |
| Cell wall perforation 1 | Lysozyme 1 mg/ml in aqua dest 20 µl dropped on | 30° C. | 10 min |
| Cell wall perforation 2 | Lysostaphin 1 mg/ml in 0.01M Tris-HCl, pH 8.0 10 µl added | 30° C. | 5 min |
| washing | Aqua dest |  | 5 s |
| drying |  | 30° C. |  |
| hybridization | Object holder + | 50° C. | 1.5 h |
|  | FISH sample mixes | 50° C. |  |
|  | 1M Tris HCl | 52° C. |  |
|  | 5M NaCl |  |  |
|  | Formamide |  |  |
|  | SDS |  |  |
|  | H₂O |  |  |
|  | DAPI |  |  |
|  | FISH probe 1, 1 pmol/ml |  |  |
|  | FISH probe 2, 1 pmol/ml |  |  |
|  | hybridization in dark, moist chamber |  |  |
| wash | aqua dest |  | 5 s |
| dry |  | 30° C. |  |
| cover | 1 drop of cover medium |  | Storage until analysis at 4° C. |
|  | (Vectashield) |  |  |
|  | position cover slide |  |  |
| microscopy | Epifluorescence microscopy with narrow band filter sets for DAPI, FITC, Cy3, Cy5 |  |  |

The invention claimed is:

1. A control preparation for use in a method for detection of a target microorganism in microbiological pathology, characterized in that
the control preparation comprises a plurality of section bodies, wherein the section bodies are joined by a joining polymer, and wherein each section body comprises a matrix polymer, and wherein
(a) a first section body comprises a first nucleic acid sequence, which is 100% identical to a nucleic acid sequence comprised in the target microorganism;
(b) a second section body comprises a second nucleic acid sequence, which in comparison to said first nucleic acid sequence, contains a deletion, an additional nucleotide or a different nucleotide in one, two, three or four positions of said second nucleic acid sequence;
wherein said joining polymer and said matrix polymer comprise, or are made of, a polymethacrylic acid alkyl ester,
and wherein the control preparation is positioned on a microscopic sample holder and each section body is positioned within the control preparation so that the identity of the section body can be identified unambiguously by its position relative to
(i) a shape of the control preparation;
(ii) a shape of said sample holder and/or
(iii) a reference point disposed on said sample holder.

2. The control preparation according to claim 1, characterized in that said first and said second nucleic acid sequence each independently of the other
(a) have a length of 12 to 30 nucleotides;
(b) are an RNA sequence;
(c) are part of a 16S, 23S, 18S or ISR-RNA sequence; and/or
(d) are present on particles or in compartments of 0.104 μm to 30 μm in size.

3. The control preparation according to claim 1, characterized in that:
each section body comprises individuals of a microorganism, with each section body having individuals of a different microorganism,
wherein said individuals are embedded into said matrix polymer, and
wherein said first nucleic acid sequence is comprised in the microorganism of said first section body and said second nucleic acid sequence is comprised in said microorganism of said second section body.

4. The control preparation according to claim 3, wherein in said section bodies single microorganism species are embedded and different section bodies are embedded in one joint bloc together with a reference body.

5. The control preparation according to claim 1, characterized in that the joining polymer and the matrix polymer
(a) comprise a common monomer unit;
(b) are made of the same monomer units, and/or
(c) are polymethylmetacrylate.

6. A method for detection of a target microorganism in a tissue preparation, comprising the steps of (a) contacting the tissue preparation with a fluorescently labelled oligonucleotide probe, wherein said oligonucleotide probe is specific for the target microorganism under conditions that allow binding of the oligonucleotide probe to a target sequence, wherein said target sequence is 100% reverse complementary to said probe, and wherein said conditions will inhibit binding of said oligonucleotide probe to a sequence that is different in one to four positions to said target sequence;
(b) contacting a control preparation according to claim 1 with said fluorescently labelled oligonucleotide probe, wherein said first nucleic acid sequence of said first section body is 100% reverse complementary identical to the sequence of said oligonucleotide probe, and said second nucleic acid sequence of said second section body in comparison to said first nucleic acid sequence, contains a different nucleoside in one, two, three or four positions of said second nucleic acid sequence;
(c) optically analysing the results of steps (a) and (b), wherein
(i) a binding of the oligonucleotide probe to the target sequence in step (a) and
(ii) a binding of the oligonucleotide probe to the first nucleic acid sequence and the absence of binding to the second nucleic acid sequence in step (b)
is interpreted as a proof for presence of the target microorganism in the sample.

7. The method according to claim 6, wherein a first and a second target microorganism of different species having the same genus are detected in a tissue, and wherein
(a) a first oligonucleotide probe is used, which is specific for the first target microorganism, and which is 100% reverse complementary identical to the first nucleic acid sequence of said first section body, and
(b) a second oligonucleotide probe is used, which is specific for the second target microorganism, and which is 100% reverse complementary identical to the second nucleic acid sequence of said second section body.

8. A kit for use in a method for detection of a target microorganism in a tissue preparation, comprising the following components:
(a) a fluorescently labelled oligonucleotide probe, wherein said oligonucleotide probe is specific for the target microorganism under conditions that allow binding of the oligonucleotide probe to a target sequence, wherein said target sequence is 100% reverse complementary to said probe, and wherein said conditions will inhibit binding of said oligonucleotide probe to a sequence that is different in one to four positions to said target sequence;
(b) a fluorescently labelled nonsense oligonucleotide probe, which does not bind to the RNA or DNA of a known microorganism under the conditions identified in paragraph (a);
(c) a control preparation according to claim 1, comprising a first nucleic acid sequence of said first section body, which hybridizes to said fluorescently labelled oligonucleotide probe under the conditions identified in paragraph (a), and a second nucleic acid sequence of said second section body, which does not hybridize to said fluorescently labelled oligonucleotide probe under the conditions identified in paragraph (a);

(d) optionally, a fluorescent dye binding unspecifically to polynucleotides, particularly 4',6-diamidino-2-phenylindol (DAPI).

9. The kit according to claim 8, comprising the following sequences:

(d) a first nucleic acid sequence selected from the group consisting of: SEQ ID NO 001, SEQ ID NO 003, SEQ ID NO 005, SEQ ID NO 007, SEQ ID NO 009, SEQ ID NO 011, SEQ ID NO 013, SEQ ID NO 015, SEQ ID NO 017, SEQ ID NO 019, SEQ ID NO 021, SEQ ID NO 023, and SEQ ID NO 025;

(e) a second nucleic acid sequence selected from the group consisting of: SEQ ID NO 002, SEQ ID NO 004, SEQ ID NO 006, SEQ ID NO 008, SEQ ID NO 010, SEQ ID NO 012, SEQ ID NO 014, SEQ ID NO 016, SEQ ID NO 018, SEQ ID NO 020, SEQ ID NO 022, SEQ ID NO 024, and SEQ ID NO 026;

(f) a fluorescently labelled oligonucleotide probe that is 100% reverse complementary to said first nucleic acid sequence.

10. A kit for use in a method for detecting and discriminating a first and a second target microorganism of different species, but of the same genus, in a tissue preparation, said kit comprising:

(a)
(i) a fluorescently labelled first oligonucleotide probe, wherein said oligonucleotide probe is specific for said first target microorganism under conditions that allow binding of the oligonucleotide probe to a target sequence, wherein said target sequence is 100% reverse complementary to said oligonucleotide probe, and wherein said conditions will inhibit binding of said oligonucleotide probe to a sequence that is different in one to four positions to said target sequence;

(ii) a fluorescently labelled second oligonucleotide probe, wherein said second oligonucleotide probe is specific for said second target microorganism under the conditions identified above (paragraph (a)(i)), (b) optionally, a fluorescently labelled nonsense oligonucleotide probe, which does not bind to the RNA or DNA of a known microorganism under the conditions identified in paragraph (a)(i);

(c) a control preparation according to according to claim 1, comprising (i) a first nucleic acid sequence of said first section body, wherein said first nucleic acid sequence hybridizes to said fluorescently labelled first oligonucleotide probe under the conditions identified in paragraph (a)(i) and wherein said first nucleic acid sequence does not hybridize to said fluorescently labelled second oligonucleotide probe under the conditions identified in paragraph (a)(i);

(ii) a second nucleic acid sequence of said second section body, which does not hybridize to said fluorescently labelled first oligonucleotide probe but with said second fluorescently labelled oligonucleotide probe under the conditions identified in paragraph (a)(i).

11. The control preparation according to claim 1, characterized in that said control preparation is shaped as a cuboid tapering or thinning on one side.

12. The control preparation according to claim 1, characterized in that (a) said first section body comprises a first nucleic acid selected from the group consisting of: SEQ ID NO 001, SEQ ID NO 003, SEQ ID NO 005, SEQ ID NO 007, SEQ ID NO 009, SEQ ID NO 011, SEQ ID NO 013, SEQ ID NO 015, SEQ ID NO 017, SEQ ID NO 019, SEQ ID NO 021, SEQ ID NO 023, and SEQ ID NO 025;

(b) said second section body comprises a second nucleic acid sequence selected from the group consisting of: SEQ ID NO 002, SEQ ID NO 004, SEQ ID NO 006, SEQ ID NO 008, SEQ ID NO 010, SEQ ID NO 012, SEQ ID NO 014, SEQ ID NO 016, SEQ ID NO 018, SEQ ID NO 020, SEQ ID NO 022, SEQ ID NO 024, and SEQ ID NO 026.

* * * * *